United States Patent
Beck et al.

(10) Patent No.: US 10,429,387 B2
(45) Date of Patent: *Oct. 1, 2019

(54) SIMPLE AND AFFORDABLE METHOD FOR IMMUOPHENOTYPING USING A MICROFLUIDIC CHIP SAMPLE PREPARATION WITH IMAGE CYTOMETRY

(71) Applicants: Markus Beck, Enschede (NL); Leon L. W. M. M. Terstappen, Amsterdam (NL)

(72) Inventors: Markus Beck, Enschede (NL); Leon L. W. M. M. Terstappen, Amsterdam (NL)

(73) Assignee: Universiteit Tweate, Enschede (NL)

( * ) Notice: Subject to any disclaimer, the term of this patent is extended or adjusted under 35 U.S.C. 154(b) by 261 days.

This patent is subject to a terminal disclaimer.

(21) Appl. No.: 15/220,695

(22) Filed: Jul. 27, 2016

(65) Prior Publication Data
US 2018/0031554 A1  Feb. 1, 2018

(51) Int. Cl.
G01N 33/569 (2006.01)

(52) U.S. Cl.
CPC .......... *G01N 33/56966* (2013.01); *G01N 2333/70514* (2013.01); *G01N 2333/70517* (2013.01)

(58) Field of Classification Search
None
See application file for complete search history.

(56) References Cited

U.S. PATENT DOCUMENTS

| | | | |
|---|---|---|---|
| 1,846,300 A | 2/1932 | Brooker | |
| 2,886,330 A | 5/1959 | Halftermeyer | |
| 2,886,449 A | 5/1959 | Ernst | |
| 3,796,217 A | 3/1974 | Arlen | |
| 5,073,857 A | 12/1991 | Peters et al. | |
| 5,077,806 A | 12/1991 | Peters et al. | |
| 5,552,279 A * | 9/1996 | Weisburg | C12Q 1/689 435/6.12 |
| 5,776,684 A * | 7/1998 | Chirikjian | C12Q 1/68 435/6.15 |
| 5,928,879 A * | 7/1999 | Dumler | A61K 39/0233 435/7.21 |
| 6,097,485 A | 8/2000 | Lievan | |
| 6,174,683 B1 * | 1/2001 | Hahn | G01N 33/54353 435/6.12 |
| 6,221,607 B1 | 4/2001 | Tsipouras et al. | |
| 6,673,533 B1 * | 1/2004 | Wohlstadter | B01L 3/5027 204/400 |
| 7,764,821 B2 | 7/2010 | Coumans et al. | |
| 7,943,397 B2 | 5/2011 | Tibbe et al. | |
| 8,189,899 B2 | 5/2012 | Coumans et al. | |
| 8,809,027 B1 * | 8/2014 | Lynch | C12Y 402/01001 435/136 |
| 9,492,376 B2 * | 11/2016 | Seliktar | A61K 9/0024 |
| 9,878,137 B2 * | 1/2018 | Desai | A61M 31/002 |
| 9,927,334 B2 * | 3/2018 | Murthy | G01N 33/54386 |
| 9,937,495 B2 * | 4/2018 | Srinivas | B01L 3/502707 |
| 9,999,596 B2 * | 6/2018 | Sinko | A61K 9/0019 |
| 10,004,828 B2 * | 6/2018 | Gazit | A61L 27/227 |
| 10,064,953 B2 * | 9/2018 | Venkatesh | A61K 31/70 |
| 10,131,901 B2 * | 11/2018 | Abrams | C12N 15/101 |
| 2004/0224380 A1 | 11/2004 | Chou | |
| 2005/0128479 A1 * | 6/2005 | Gilbert | G01N 15/1459 356/338 |
| 2009/0079963 A1 | 3/2009 | Ermantraut et al. | |
| 2009/0220968 A1 * | 9/2009 | Issadore | B01L 7/52 435/6.11 |
| 2010/0179068 A1 | 7/2010 | Kaiser et al. | |
| 2012/0028811 A1 * | 2/2012 | Craighead | B01L 3/502753 506/1 |
| 2012/0064041 A1 * | 3/2012 | Alexanian | A61K 35/28 424/93.7 |
| 2012/0307244 A1 * | 12/2012 | Sharpe | G01N 15/1012 356/338 |
| 2013/0213811 A1 * | 8/2013 | Kennedy | G01N 33/54386 204/455 |
| 2014/0038230 A1 * | 2/2014 | Beck | G01N 1/28 435/39 |
| 2014/0087971 A1 * | 3/2014 | Kiesel | G01N 21/6452 506/12 |
| 2015/0316483 A1 * | 11/2015 | Deans | G01N 21/76 506/12 |
| 2017/0241874 A1 * | 8/2017 | Lee | G01N 1/31 |

OTHER PUBLICATIONS

Graham and McNeil, "Hydrogels for Controlled Drug Delivery", Biomaterials, 1984, vol. 5, pp. 27-38.
Rodriguez et al, PLoS Med., Jul. 2005: 2(7): e182.
Merle and Speiser, J. Pharm Sci, 62. 1444-1448 (1973).
Young et al., J. Controlled Release 109, Issues 1-3,Dec. 5, 2005, pp. 256-274.
Hessel et al, Chem Eng Sci 60, 2479-2501 (2005).
Nguyen and Wu, J. Of Micromech and Microeng 15R1, doi:10, 1088/0960-1317/15/2/R01 (2005).
Tabata and Ikada, Advanced Drug Delivery Reviews, (31) 1998, 287-301.
Moon (2009) Biosensors and Bioelectronics, v24, p. 3208-3214.

* cited by examiner

*Primary Examiner* — Ann Y Lam
(74) *Attorney, Agent, or Firm* — Joseph F. Aceto, Esq.

(57) ABSTRACT

The system includes a simple system for CD4 and CD8 counting in point-of-care HIV staging within resource poor countries. Unlike previous approaches, no sample preparation is required with the sample added directly to a chip containing dried reagents by capillary flow. A large area image cytometer consisting of an LED module is used to excite the fluorochromes PerCP and APC labeled targets and a monochrome CCD camera with a combination of two macro lenses captures images of 40 mm$^2$ of blood (approximately 1 microliter). CD4 and CD8-T-lymphocyte counts correlate well with those obtained by flow cytometry. The cytometer system described in the present invention provides an affordable and easy-to-use technique for use in remote locations.

6 Claims, 7 Drawing Sheets

SIMPLE AND AFFORDABLE METHOD FOR IMMUOPHENOTYPING USING A MICROFLUIDIC CHIP SAMPLE PREPARATION WITH IMAGE CYTOMETRY

CROSS-REFERENCES

This application is a divisional application of U.S. Ser. No. 13/817,180, filed 24 Oct. 2013, which is the National Stage application under 35 U.S.C. 371 of PCT International Application No. PCT/US2011/035667, filed 8 May 2011, which claims priority from Provisional patent application Ser. No. 61/332,763, filed 5 Aug. 2010, the contents of which are hereby incorporated by reference in their entirety.

FIELD OF THE INVENTION

This invention relates generally to image cytometry, enumeration of microscopic particles distributed within a microfluidic chip, and methods for automatic sample preparation inside the microfluidic chip. The combination of novel sample preparation techniques in thin counting chambers with large-area image cytometry based on excitation spectroscopy are key to the realization of a simple and robust test for the enumeration of fluorescently labeled cells in whole blood. The present invention is applicable in the analysis of specific sample characteristics such as, but not limited to, CD4 and CD8 counting for point-of-care HIV staging in resource poor countries.

BACKGROUND OF THE INVENTION

The enumeration of absolute levels of cells and their subsets in body fluids is of primary importance in determining the state of health of human beings and mammals in general. The primary analytical platform for performing such analyses is flow cytometry in which the specimen is either injected directly or after prior enrichment in rare cell analysis. Flow cytometry and similar complex analytical systems remain largely inaccessible for routine clinical use in resource-poor countries due to high instrument and reagents costs, lack of technical support, lack of robustness requiring frequent service, and the need for AC power. There is a clear need for simpler, more compact and less expensive systems also operable with emergency DC battery power and preferably exhibiting comparable performance characteristics.

In addition to the above-cited full sized flow cytometry systems available for example from Becton Dickinson and Beckman-Coulter, these vendors also sell scaled down less expensive versions, which still suffer from the other cited limitations. Similar limitations apply to the compact CyFlow® from Partec GmbH, (Munster, Germany) and to the Guava Personal Cytometer (Burlingame, Calif.). U.S. Pat. No. 6,097,485 (assigned to Integrated Wave Guides, Brookings, S. Dak.) discloses an ultra-miniature personal flow cytometer (pFCM) claimed to be of lower cost, but still exhibiting rather complex electronic circuitry, optical designs, data reduction, all of which contribute to unacceptable complexity for a third world setting. All these systems use the flow concept, which obviously complicates the instrumental design. These scaled down versions of flow cytometry systems do not meet the clear need for a truly simple, compact, rugged, battery-operable and affordable cell analyzer.

Among the numerous clinical applications for a simple cell analyzer are: counting of CD4 T-lymphocytes in HIV, B-lymphocytes in Chronic Lymphocytic Leukemia, CD34 progenitor cells, granulocytes and platelets in patients treated with chemotherapy, and leukocytes in blood bags. The current systems and methods for cell analysis have some significant disadvantages. They generally require sophisticated techniques, which involve the use of instruments that are expensive both in terms of initial cost and maintenance as well as requiring highly trained personnel. This makes the conventional systems unsuitable for use in laboratories of resource-poor countries or physicians' offices. Therefore, a low-cost, easy-to-use method for cell enumeration such as CD4 enumeration is needed. Such a method may serve as a compact alternative to the current cell analysis systems that would be suitable for physician practices, bedside testing, or in open field settings with the ability to count rare cells in each condition. Further enumerating white cells in, for example, blood bags by a rapid, inexpensive means, instead of using flow cytometry where the analysis time is very long.

The invention described herein meets the criteria above. The system does not require extensive sample preparation. Preparation is achieved by adding a sample through capillary flow to a chip containing reagents in a dried hydrogel layer. A large-area image cytometer with three light sources for the excitation of different fluorochromes and a CCD camera is used as the imaging platform. The prior art contains computer-assisted microscopes. U.S. Pat. No. 5,018,209 teaches a computer driven microscope in which the user manually selects positive events while looking at an image. Obviously, this does not have a high enough throughput to be an effective analyzer, especially in remote settings.

In U.S. Pat. No. 5,287,272, an automated cytological specimen classification system and method is described. This system relies on a complicated neural network to process images of cells based on morphology. While very effective for classifying objects in images, it requires a large amount of computational resources. Furthermore, human input and subsequent analysis is still necessary. Other devices, such as those described in U.S. Pat. Nos. 5,073,857 and 5,077,806, use window sub-image pixel counting algorithms for image analysis by using predetermined thresholds.

Another set of instruments in the prior art is designed as bench top analyzers. In U.S. Pat. No. 5,073,857, pap smears are analyzed by a computer controlled microscope and camera and computer driven image analysis. In U.S. Pat. No. 6,221,607, an automated microscope is described for analyzing in situ hybridization events in a biological specimen.

The devices in the aforementioned prior art are designed to image slides. None are capable of detecting and enumerating a target population within a biological specimen as defined herein. Furthermore, none appear to be portable or high throughput devices. These instruments are designed to rely on a desktop computer to control the microscope and camera, and to perform image analysis. The present invention overcomes many of the difficulties that lie in the prior art.

In US Patent Applications 20100179068 & 20090079963 Clondiag GmbH/Alere GmbH, Jena, (Germany) disclose an instrument and method for point-of-care CD4 counting. Other than the on-chip sample preparation method we disclose here, their test requires active mixing since the reagents are contained in a pellet inside the chamber and therefore do not mix with the sample by diffusion on a useful time scale. The image area is only 1727 μm×1385 μm and the height of the chamber is 0.04 mm, i.e. the volume of sample per image is less than 0.1 μl. Since this is not sufficient for many applications, images of several distinct portions of the sample have to be taken. This can be realized by moving the image area (e.g. by moving the camera) or by moving the sample, either by displacing the whole chamber or by pumping the sample through the chamber. Any of these solutions will increase the complexity of the system compared with the invention we disclose here.

William R. Rodriguez et al. developed another approach for CD4 enumeration based on fluorescence imaging, which has been further developed and produced by LabNow (PLoS Med. 2005 July; 2(7): e182.). This approach uses filters in order to separate leukocytes from erythrocytes. Other than in the method we disclose here, the sample preparation has to be done manually and the exact volume of the blood sample has to be known.

Hydrogels have been used for several decades for the controlled release of molecules. In 1959, several patents U.S. Pat. Nos. 2,886,440-2,886,449 by Gen Foods Corp disclosed the use of gelatin to control the release of flavor from chewing gum. From the 1970s, drug release from gels was studied (U.S. Pat. No. 3,796,217; H. P. Merle and P. Speiser, "Preparation and in vitro evaluation of cellulose acetate phthalate coacervate microcapsules", J. Pharm. Sci. 62, 1444-1448, (1973)). A review article published in 2005 (S. Young et al., "Gelatin as a delivery vehicle for the controlled release of bioactive molecules", J. Controlled Release 109, Issues 1-3, 5 Dec. 2005, Pages 256-274) lists many applications for the release of molecules from gelatin. None of these applications are related to in vitro diagnostics or microfluidics. An earlier, similar review article neither includes any application comparable to the invention we disclose here: N. B. Graham and M. E. McNeill, "Hydrogels for controlled drug delivery", Biomaterials 5, 1984, Pages 27-36.

The possibility to control chemical reactions by diffusion of reagents through a gelatin layer has been known for a long time. It is also the principle underlying the developing and fixation processes of photographic material. See for example U.S. Pat. No. 1,846,300. However, to the best of our knowledge, the controlled release of reagent molecules from hydrogels for diagnostics application in a geometrical configuration that avoids the necessity for additional active mixing has not been disclosed previously.

Due to the small dimensions inside microfluidic devices, flow will usually be laminar. Turbulent flow is difficult to realize in microscopic structures. Therefore, ways to realize efficient on-chip mixing have been of interest over many years. Several recent articles review different solutions for this problem (V. Hessel et al., "Micromixers—a review on passive and active mixing principles", Chem. Eng Sci 60, 2479-2501 (2005), and N.-T. Nguyen and Z. Wu, "Micromixers—a review", J. of Micromech. and Microeng 15 R1, doi: 10.1088/0960-1317/15/2/R01 (2005)). The possibility to distribute the reagent inside the device and to slow down the release/mixing of reagents in order to ensure homogeneous concentrations throughout the whole sample is not considered in any of the publications.

SUMMARY OF THE INVENTION

This invention describes a simple sample preparation method, fluidic chip design, compact electronic optical instrument, and related analytical methods for the detection and enumeration of target cells or particles. A fluid sample, such as whole blood, is introduced by capillary flow into the reaction chamber of a microfluidic chip. The reaction chamber is coated on the inside with a dried hydrogel containing fluorescently labeled antibodies. Different antibodies are generally (but not necessarily) linked to different fluorescent dyes, such as Peridinin Chlorophyll Protein (PerCP) and Allophycocyanin (APC). The cells of interest or target cells in the blood sample are labeled by incubation with monoclonal antibodies specific for the target cell, such as CD4 and CD8 for counting T-lymphocytes in blood. During the filling of the chamber with blood, the hydrogel maintains the distribution of the fluorescently labeled antibodies. After the filling, the hydrogel begins to take up fluid from the sample and swells, thereby allowing the antibodies to interact with their targets. Without the hydrogel, the antibodies would mix with the sample immediately, which would result in a non-uniform distribution of the antibodies after the filling is complete. After incubation, the fluorescence is imaged with a CCD camera. Automated image analysis provides the cell concentrations.

Compared with previous image cytometry approaches, three main innovations make the test simpler, cheaper and more robust. First, the optical system in the image cytometer is simplified by the choice of APC and PerCP as fluorochromes. Since one common wavelength range for fluorescence emission can be used, chromatic aberrations do not affect the results and no filter changer is needed. Second, the combination of large-area (>40 mm$^2$) imaging with a very thin counting chamber (~25 µm) ensures sufficient sample volume without the need for sample dilution or red blood cell lysis. As a consequence, no precision is needed during the sampling of blood, since the measured sample volume is given by the area imaged by the camera system and the height of the counting chamber.

Third, and most important, the sample preparation is simplified through the dried reagent layer on the microfluidic chip, which does not require any active mixing, since diffusion across the 25 µm chamber height is sufficient.

The present invention provides a system with inexpensive components for a very simple approach for CD4 and CD8 T-lymphocyte counting. The prototype of our instrument will fit into a backpack, including space for 500 tests. It will weigh less than 5 kg, including a battery pack and computer. Total power consumption will be less than 50 Watts (peak) and 25 Watts average. Because of the simplicity and minimal technical training required for the operator, the system and device is particularly useful for rural areas in developing countries.

It is to be understood and appreciated that these discoveries, in accordance with the invention, are only illustrative of the many additional potential applications of the apparatus, methods and algorithms that may be envisioned by one of ordinary skill in the art, and thus are not in any way intended to be limiting of the scope of the invention. Accordingly, other objects and advantages of the invention will be apparent to those skilled in the art from the following detailed description, together with the appended claims.

DETAILED DESCRIPTION OF THE PREFERRED EMBODIMENTS

The number of CD4+ T-lymphocytes in blood is a good indicator for the effectiveness of antiretroviral therapy (ART) of patients infected with the human immunodeficiency virus (HIV). For infants infected with HIV a CD8+ T-lymphocytes count is also acquired as the ratio of CD4 and CD8 better reflects the disease status. In most parts of the world, flow cytometry is successfully applied to carry out these tests. However, rural areas, for example in Sub-Saharan Africa, the region most affected by HIV, do not have access to CD4 counting as they often lack the necessary infrastructure to ship cooled blood samples to central labs and get the result back to the patient. Accordingly, there has been a large effort over the last decade to develop an affordable, portable test that can be carried out with minimal training requirements. A single platform image cytometer was previously described that simplified the instrumentation, but still required precision for the sample preparation, which frequently can not be met in the field by less experienced operators (see U.S. Ser. Nos. 10/903,798, 11/434,321 and 12/707,578, the entire disclosures are incorporated by reference into the present specification). Automated sample preparation is possible (e.g. in the "PointCare NOW" instrument of PointCare Technologies Inc, Marlborough, Mass., USA), but the ambient conditions to be expected during operation (high temperature, large temperature differences, humidity ranging from almost 0% to 100%) impose enormous challenges on the long-term stability of such a system.

The system described in the present invention does not require any precision during sample preparation since the sample volume is given by the dimensions of a microfluidic chip containing the dried reagents for cell staining and the image area of the imaging system. For CD4 and CD8 counting, combinations CD3-APC/CD4-PerCP and CD3-APC/CD8-PerCP, respectively, are used in separate test chambers. These chambers are filled with whole blood by capillary flow and after an incubation time of 30 min, the fluorescence is imaged with a CCD camera. Automated image analysis provides the results within 5-20 seconds and can be performed on a standard computer.

On-Chip Sample Preparation

Figure 1:
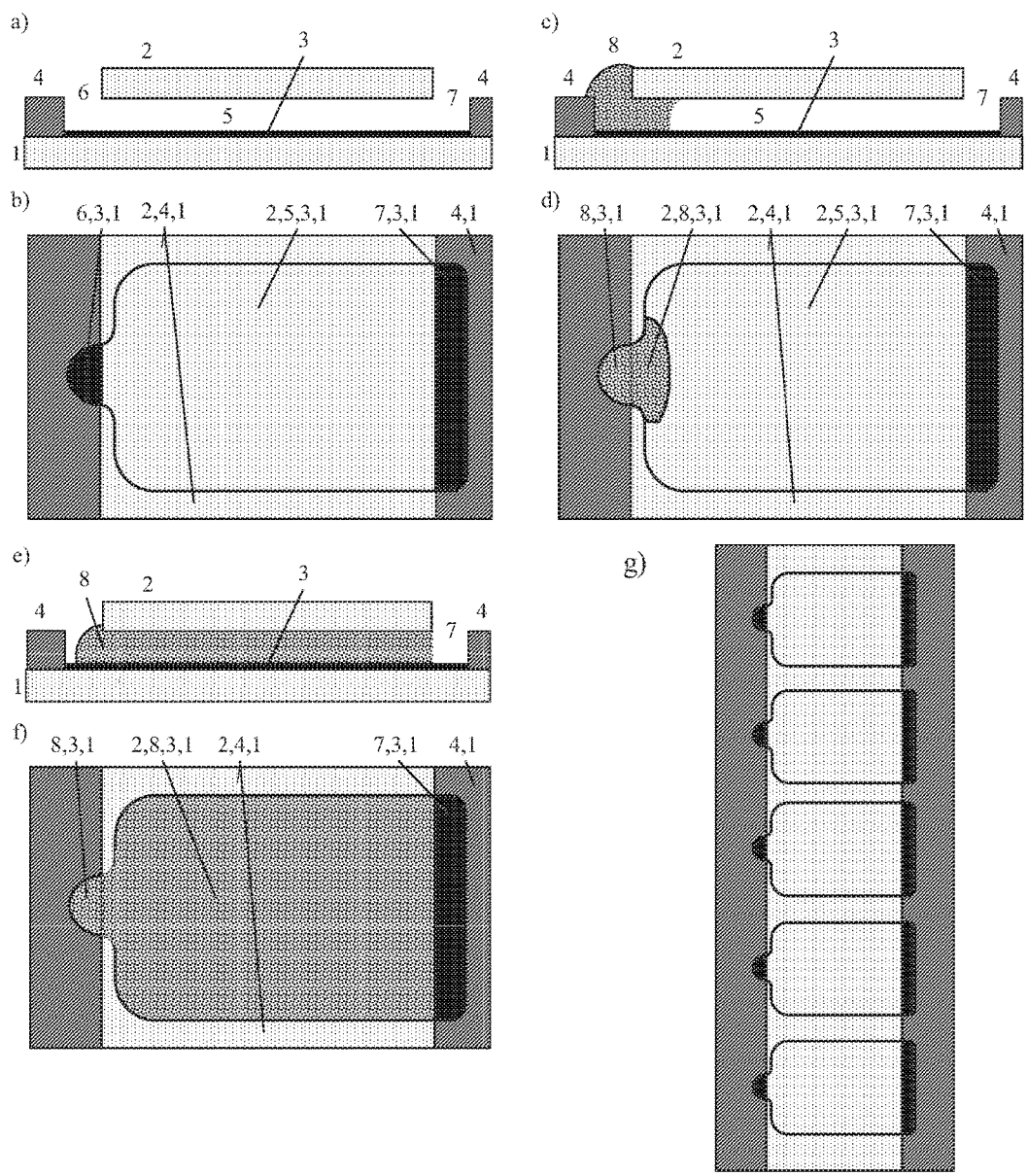
FIG. 1 is a schematic illustration of the fluidic chip and filling by capillary flow (a,b) Cross section and top view of the fluidic chip (counting chamber) before use; (c,d) Cross section and top view of the fluidic chip (counting chamber) during the filling process with the sample (e,f) Cross section and top view of the fluidic chip (counting chamber) filled with sample (g) One possible embodiment with five counting chambers in between two standard-size microscope slides, where one of them has been cut in half.
Figure 2:
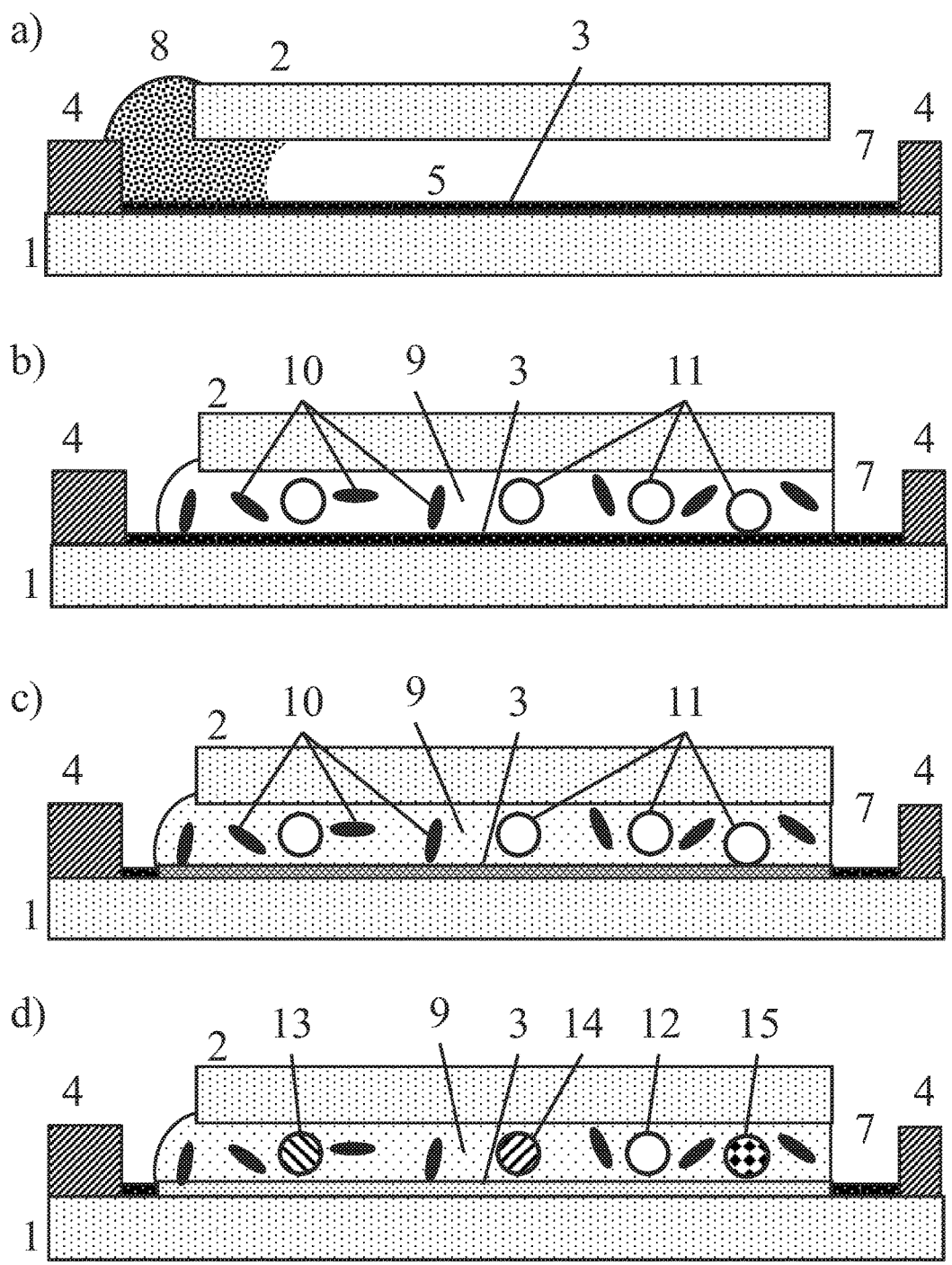
FIG. 2 is a schematic illustration of the on-chip sample preparation (example: leukocyte staining) (a): Cross section of the fluidic chip (counting chamber) during the filling process with blood; (b) Illustration of the blood components (9: blood serum, 10: erythrocytes, 11: leukocytes) immediately after the filling of the chip with blood; (c) Release of the reagent from the reagent layer (after the filling has completed, typical time scale: 10 s-10 min). (d) Stained leukocytes can be distinguished after the incubation time (typically 5 min-60 min).
Figure 3:
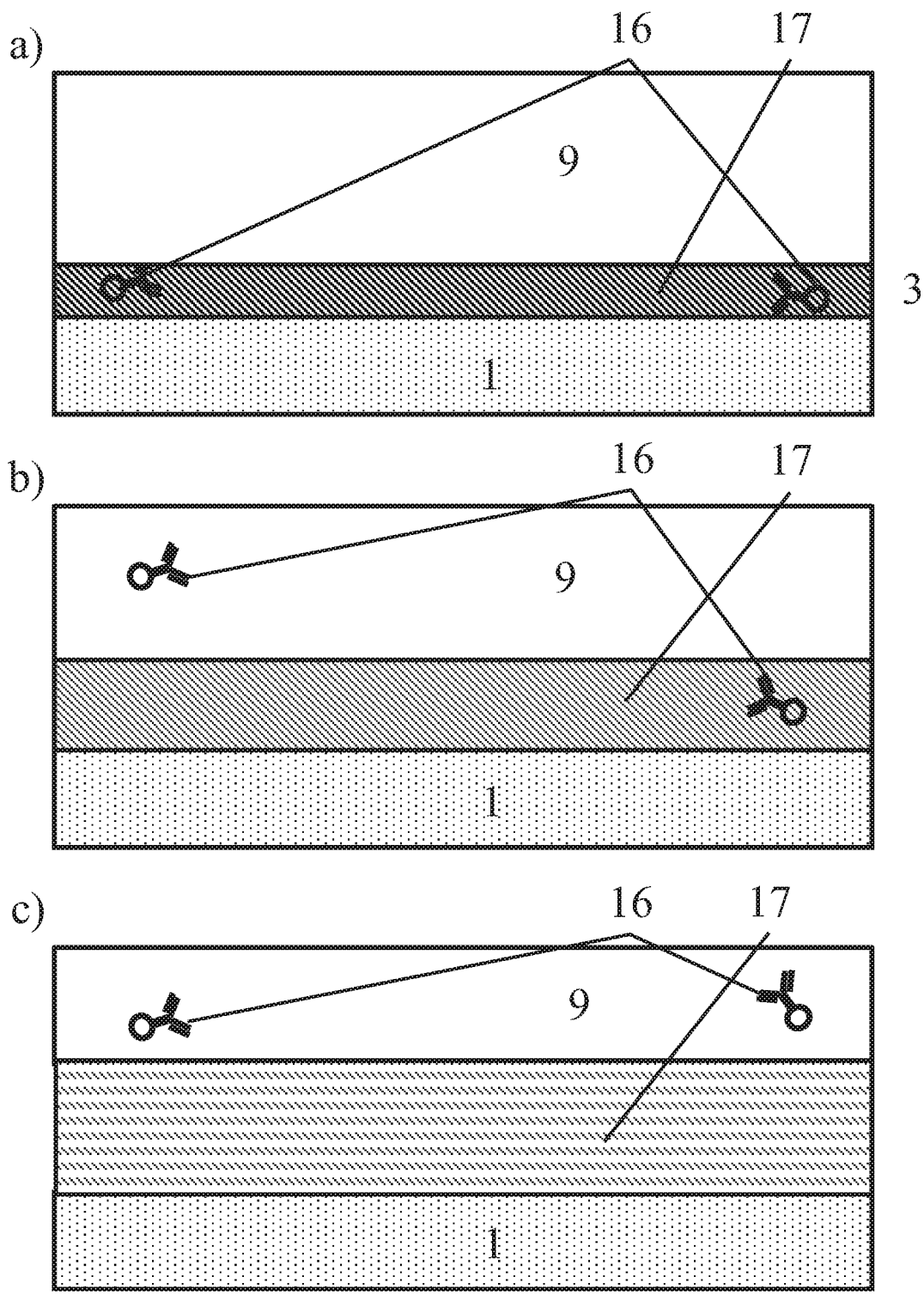
FIG. 3 is an illustration of the processes in the reagent layer for one possible embodiment: (a) During the filling, the reagent molecules (here drawn as fluorochrome-conjugated antibodies) stay within the layer (typically 0.5 s-5 s); (b) After the filling, the layer material (e.g. a hydrogel) takes up fluid from the sample, swells and starts to release reagent molecules (typically 10 s-1 min). (c) Most of the reagent molecules have been released (typically 1 min-10 min).
Figure 4:
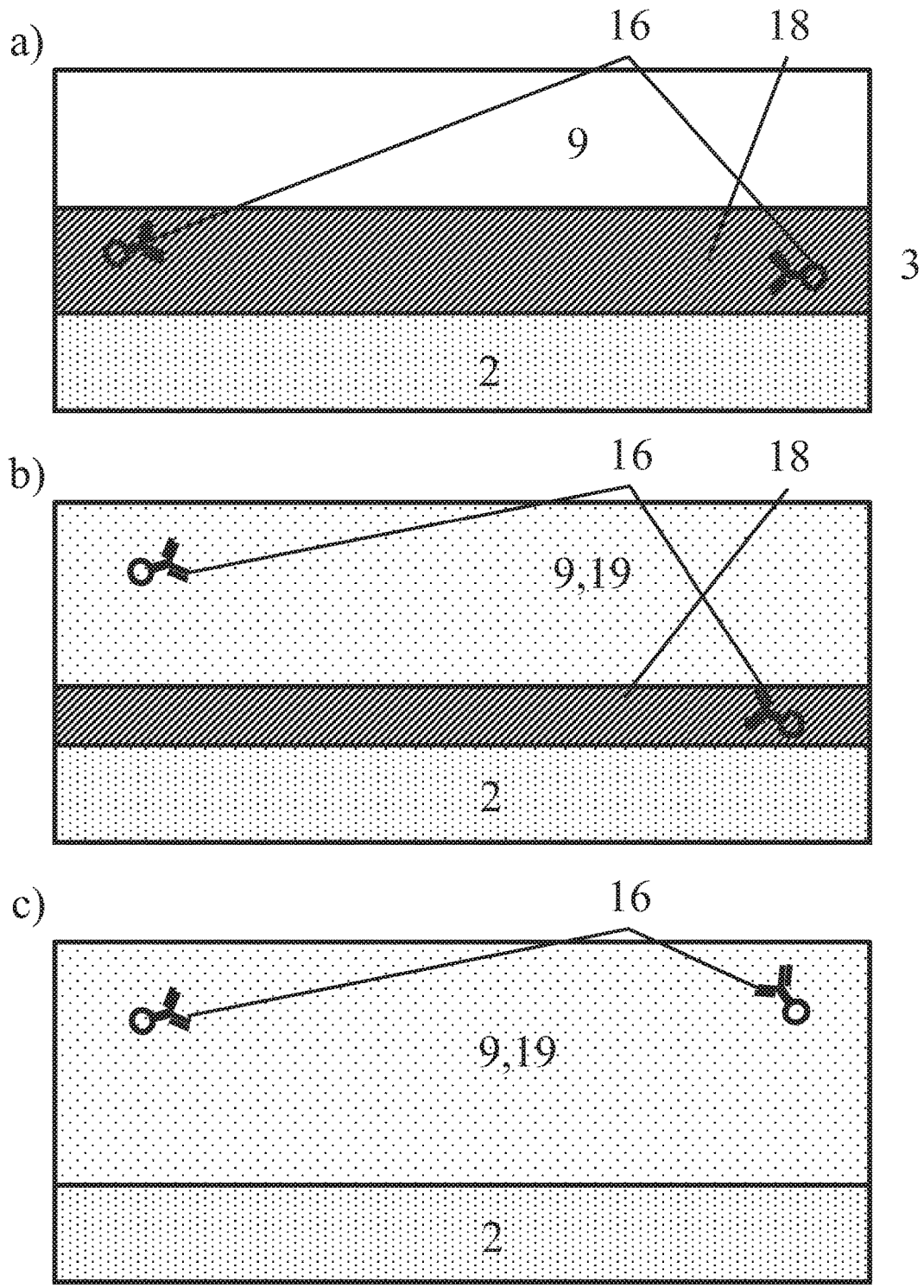
FIG. 4 is an illustration of the processes in the reagent layer for an embodiment different from the one of FIG. 3: (a) During the filling, the reagent molecules (here drawn as fluorochrome-conjugated antibodies) stay within the layer (typically 0.5 s-5 s); (b) After the filling, the layer material starts dissolving in the sample fluid and thereby to release reagent molecules (typically 10 s-1 min). (c) The layer material has dissolved and the reagent molecules together with the layer material have been released into the sample fluid (typically 1 min-10 min).

FIG. 1 illustrates the geometry of the microfluidic counting chamber of the present invention and the filling by capillary flow. FIG. 1a) is a cross section through the device. The chamber volume 5 is given by the space between two chamber walls 1, 2 (of which at least one is optically transparent if the detection principle relies on optical imaging methods) separated by a spacer material 4, which defines the lateral boundaries of the chamber volume. In one embodiment, the chamber walls are glass microscope slides, the spacer material is 25 μm thick laminating adhesive, and the lateral chamber boundaries are defined by shapes cut from the laminating adhesive. Other fabrication methods for microfluidic devices can be used, which include the possibility that, instead of using a spacer material, the chamber volume is formed into the material of one or both chamber walls, e.g. by injection molding, imprint lithography, or etching. At least one of the chamber walls is coated with a reagent layer 3 (for example a hydrogel such as gelatin or similar compound) containing labeling reagents such as fluorescently labeled antibodies. The coating can cover the whole surface of the chamber wall or can be restricted to the detection area, which can be sub-divided into areas with different reagent coatings. The coating can be a homogeneous layer, but can also have gaps, provided that the gaps are not much larger than the diffusion length of the reagent molecules during the incubation time. FIG. 1b) shows the top view of the chamber, where the sequences of the numbers indicate the parts of the design from top to bottom. FIGS. 1c), 1d) show the chamber during the filling process. The chamber volume 5 has an opening 6, which is used to fill the chamber with the sample 8. The filling is preferably realized by capillary flow, but active pumping is also possible. A second opening 7 can be used to let out the substance (e.g. air), which is present before the filling of the sample. The sample can be whole blood, obtained through venipuncture, from a finger prick or similar methods. In one embodiment using capillary flow, the filling process stops when the sample reaches the second opening 7 (see FIGS. 1e), 1f)). FIGS. 2, 3, 4 illustrate the sample preparation method. FIG. 2 illustrates the cell staining for one embodiment where the sample 8 is whole blood consisting of blood serum 9, red blood cells (erythrocytes) 10 and white blood cells (leukocytes) 11. FIGS. 2b) and 3a) show, respectively, the cross section of the chamber filled with blood (size of cells not to scale) and the reagent layer 3 consisting of layer material 17 and reagent particles 16 (indicated as fluorochrome-conjugated antibodies; size not to scale) in between a chamber wall 1 and the chamber volume 5 filled with sample fluid 9, immediately after the filling. As indicated in FIGS. 2c) and 3b),c), after completion of the filling process, the reagent layer swells by taking up sample fluid 9 (e.g. blood serum).

After the staining process, different phenotypes 12, 13, 14, 15 can be distinguished, as indicated in FIG. 2d). While FIG. 3 illustrates the release mechanism for one embodiment, where the reagents are released from a layer, FIG. 4 illustrates a different embodiment where the layer material 18 dissolves after the filling and thereby releases the reagent particles. In this case, dissolved layer material 19 mixes with the sample fluid 9. In some embodiments, a combination of both processes (release from layer and dissolution of the layer) may occur. For example, gelatin dissolves only very slowly at temperatures below 40-50° C. and much faster at higher temperatures. The predominant release mechanism can in this case be influenced by the temperature. During the filling of the microchip, the reagent particles 16 stay within the layer material (17 or 18) so that the initial uniform lateral distribution of reagent is maintained. Release of the reagent during the filling of the chip would result in washing of the reagent towards the far end of the chamber 7 and, depending on size and weight of the reagent molecules, would not distribute uniformly across the layer by diffusion during the incubation time. Thus, the release of the reagent during the filling needs to be avoided.

Two Preferred Embodiments: CD4 Counting and CD8 Counting

General Considerations

In two preferred embodiments, the reagent layer is a gelatin coating containing monoclonal CD4 and CD3 (or CD8 and CD3) antibodies conjugated with PerCP and APC, respectively. Within a time longer than the filling and shorter than the incubation, i.e. several seconds to a few minutes, the blood serum penetrates into the layer, causing it to swell and release the antibodies. Subsequently, cell staining with fluorescently labeled antibodies takes place as in any other immunofluorescent staining. According to the Einstein-Stokes equation, the diffusion constant of particles in a fluid is given by $$D = \frac{k_B T}{6\pi \eta r},$$

where $k_B$ is Boltzmann's constant, T is the absolute temperature, $\eta$ is the viscosity of the fluid and r is the hydrodynamic radius of the particles. The diffusion time $T_D$ it takes for the antibodies to diffuse across the 25 μm channel height can be estimated as follows. The hydrodynamic radius of fluorochrome-labeled antibodies is typically the range 5 nm-10 nm, the viscosity of blood at 37° C. is about $4 \times 10^{-3}$ N s/cm², the incubation temperature is 37° C.=310K. This yields a diffusion constant of roughly D=0.5 . . . $1 \times 10^{-11}$ m²/s. In other words, the diffusion length during the incubation time $T_{inc}$=1800 s is $L=\sqrt{DT_{inc}} \approx 90$ . . . 140 μm. Accordingly, $T_D = d^2/D \approx 125$ . . . 250 s. These rough estimates demonstrate that mixing by diffusion is possible within a few minutes in the chambers used in the described embodiment.

As in a hemocytometer, the sampled volume will depend on the height of the chamber and on the imaged area. Since both parameters are controlled precisely during the fabrication of instruments and microfluidic chips, no precision is needed during sampling and instrument operation. The numerical aperture of the imaging system is preferably chosen such that the depth of focus is lager than the height of the chamber and smaller than the total height of the fluidic chip. Thereby, objects inside the chamber are in focus and objects (contaminants) on the outside of the chip are out of focus. At the same time, the alignment between camera and fluidic chip should not be too critical in a low-cost instrument. We therefore choose a numerical aperture of about 0.05, which corresponds to a depth of field of about 300 μm and the diffraction limit for the wavelength range of the fluorescence light (680 nm) is about 8 μm. This estimate together with the estimate of the reagent diffusion demonstrates that the range of suitable parameters is rather limited and that the described configuration may be close to optimum for the described application. For applications where robustness and low costs are less important, we would choose a larger NA, which would improve image quality, but more expensive optics would be required and alignment would become more critical. For applications with lower optical absorption by the sample and lower concentrations of cells, we would choose a thicker counting chamber.

To summarize, the following conditions have to be fulfilled:

The optical transmission of excitation and emission light through the counting chamber filled with sample should be at least ~10%, preferably >30%. This condition limits the maximum thickness of the chamber, depending on the absorption characteristics of the sample and the fluorescent labels used in the assay. Mainly limited by the optical absorption by hemoglobin, for whole blood, the maximum thickness varies between about 10 μm for green light and a few millimeters for wavelengths >650 nm. In one embodiment, we use red (600 nm-630 nm) and blue (440 nm-500 nm) excitation light and fluorescence emission wavelengths between 650 nm and 710 nm. The optical absorption of the blue excitation light by blood (mainly by hemoglobin) limits the chamber thickness to about 50 μm.

The whole chamber has to be within the depth of field of the imaging system. At the same time, the optical resolution should be sufficient to distinguish between single cells and closely spaced cells. This condition sets upper and lower boundaries on the numerical aperture (NA) of the imaging optics. To resolve single cells (~10 μm optical resolution), NA has to be larger than ~0.04 (diffraction limit). Since a larger NA results in a smaller depth of field, the upper boundary for NA is determined by the thickness of the counting chamber (or vice versa). This limits the chamber thickness to about 500 μm. However, in order to detect the fluorescence efficiently, a larger NA is desirable, which requires a smaller chamber thickness. A useful range for the enumeration of CD4+ T-cells in whole blood is NA=0.03 . . . 0.1. With very high quality, expensive optics, large areas can be imaged with high NA. This could be advantageous for high-end laboratory equipment, but for the purpose of point-of-care diagnostics, this is currently not an option.

The diffusion time of the reagent molecules across the chamber height (if both sides of the chamber are coated with a reagent layer: across half the chamber thickness) should be within an acceptable range. In the case of CD4 counting, up to 1 hour incubation time may be acceptable. Preferably, the incubation time should be no longer than 30 min. For useful concentrations of antibodies, the antibody-antigen binding takes about 10 min-30 min. Therefore, the diffusion time of the antibodies across the chamber should be no longer than about 10 min. This limits the chamber thickness to about 50-100 µm if one of the chamber walls is coated, 100-200 µm if both sides are coated.

The minimum sample volume is given by the concentrations of the cells of interest in the sample and the acceptable statistical error. In the case of CD4 counting, treatment decisions are based on cell concentrations in the range 100-500 cells per µl. If 10% uncertainty is acceptable, at least 1 µl has to be tested. If this volume is to be captured in one image, this condition determines the minimum image field. For a 25 µm thick counting chamber, this area is 40 mm².

Microchip Fabrication

The microfluidic chambers are built from standard microscopy slides (Menzel Glaser, 25 mm×76 mm), laminating adhesive (3M, 501FL, nominal thickness 1 mil (25.4 µm)), gelatin (type A, Sigma Chemical, bloom approx. 300), and antibody solution (Exbio; CD4-PerCP: Mouse IgG1, clone MEM-241; CD8-PerCP: Mouse IgG2a, clone MEM-31). The shape of the microfluidic chambers (8 mm×12 mm+inlet section) is cut from laminating adhesive, which is then attached to a microscope slide together with the plastic liner of the tape as illustrated in FIG. 1. One or several (e.g. five as shown in FIG. 1g) chambers can be fabricated on one slide.

A gelatin solution of 0.15% (wt) gelatin is prepared by dissolving gelatin type A from stock in micro-filtered deionized (milliQ) water at 40° C. We then add CD4-PerCP or CD8-PerCP solution and CD3-APC solution from stock to obtain antibody concentrations in the range of ~1 to ~5 nM/l (or ~2×10$^9$ to ~10$^{10}$ antibodies/µl) with all reagents at room temperature. This solution is sonicated for approximately 5 seconds to dissolve aggregated antibodies and spun at 11,000 rpm for 10 min to remove remaining larger aggregates of antibodies. The areas that were cut into the tape previously are filled with 15-20 µl of the reagent solution. After drying, the slides are dipped for 10 seconds into milliQ water at room temperature to remove the antibodies, which are quickly released from the reagent layer. Antibodies in smaller pores within the collagen network of the gelatin and antibodies, which are not close to the surface of the layer will remain. To prevent further release of antibodies, the layer is dried quickly (within a few seconds) using dry air. The nominal thickness of the layer is approximately 150 nm, assuming that the gelatin is dry (0% water) and compact. The tape liner is removed and the cover, a microscope slide cut in half (12.5 mm×76 mm), is attached to define the chamber. Using interferometry the thickness of several chambers both with and without the reagent layer has been measured with a precision of about 250 nm. The measured chamber thickness is 26.5 µm±1 µm. Differences in chamber thickness between coated and uncoated slides were insignificant since the resolution of the measurement was not sufficient and due to the variation of the thickness of the adhesive.

Choice of Fluorochromes

Typical immunofluorescent protocols use fluorochromes with different emission wavelengths to identify the staining of the cells labeled with different antibodies. This works well in flow cytometry because of the time resolution of the instrument. Since there is only one cell at a time in the excitation spot(s), events on different detectors can easily be attributed to the same object (cell). Because the flow speed is controlled precisely, this also works for several excitation spots. However, image cytometry is typically done without time resolution (exception: e.g. laser scanning cytometry). Therefore, a good overlay between the images corresponding to different emission wavelengths is required. Using automatic filter changers requires high precision in manufacturing and assembly of the components, but even a very small offset between images can be critical with the low magnification used in the present invention. Furthermore, the chromatic aberration of the imaging optics can be problematic. Alternatively, a chromatic beam splitter can be used to image different emission wavelengths onto different image sensors, as in 3-chip (typically 3-CCD, but also 3-CMOS) cameras. Affordable cameras for the consumer market typically have rather low resolutions and the chromatic beam splitters do not meet the requirements of fluorescence imaging.

With the combination of the fluorochromes PerCP and APC, the need to image two different emission wavelengths is eliminated. This is possible because their emission spectra have a large overlap, with maxima in the far red spectral range at 670 nm and 685 nm, respectively, while their excitation spectra have only very little overlap with maxima at 480 nm and 630 nm, respectively. Therefore, PerCP and APC can be distinguished taking two images through the same emission filter with red and blue excitation light, respectively. This reduces complexity and costs because the alignment of excitation light is less critical than the alignment of two images. Further, high-power LEDs are available at lower costs than high-resolution image sensors or high quality interference filters. As described below, the excitation module contains three LEDs, red, green and blue. Therefore, a third fluorochrome could be used which is excited mainly by green light. Examples are Nile Red, the tandem conjugates PE-Cy5, PE-Cy5.5, or the nucleic acid dye 7-AAD. The considerable overlap between the excitation spectra could be problematic, but compensation can be applied.

Imaging Setup

Figure 5:
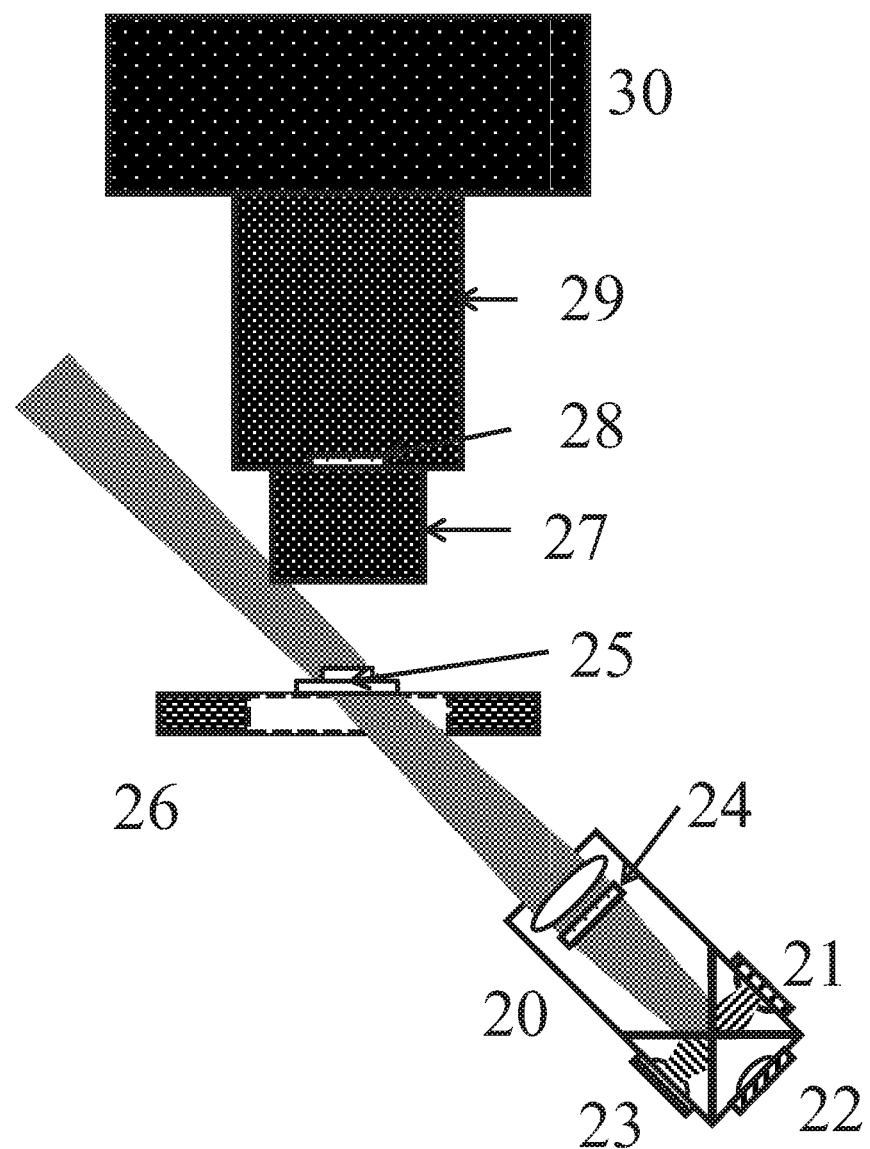
FIG. 5 is a schematic illustration of the imaging setup, consisting of an excitation module 20 with LEDs 21-23, optical filters 24, 28, a sample holder 26, a sample 25, imaging optics (27, 29) and a camera 30.

A schematic representation of the image cytometer is illustrated in FIG. 5. It consists of an LED excitation module 20 with three light emitting diodes (LEDs) 21, 22, 23, a microscope slide holder 26 and a monochrome CCD camera 30 (SBIG, ST-1603ME, with 1530×1020 9 µm square pixels, sensor size: 13.8 mm×9.2 mm) with a combination of two macro lenses 27, 29. The excitation module is taken from a video projector (Samsung SP-P410ME 800×600 DLP LED ultra-portable projector). The contained 5.4 mm² red, green and blue LEDs were replaced by 4.0 mm² LEDs from the same manufacturer (Luminus Devices, Phlatlight CBT-40 Series (red: $P_{opt}$~1.6 W, green: $P_{opt}$~1.2 W, blue: $P_{opt}$~2.2 W)) to reduce power consumption and heat generation. The LEDs are in good thermal contact with a copper block for cooling. The module contains a collimation lens for each LED and combines the optical paths of the three colors with dichroic beam splitter plates. Through a 650 nm short pass filter 24 (Semrock, FF01-650/SP-25) and a lens (f~30 mm, part of the LED projector), the LED areas are projected with about 3.5× magnification towards the imaging area. Since the optical path of the excitation light is tilted approximately 45° with respect to the image plane, this image is distorted and therefore has a slightly non-uniform intensity distribution across the image area. However, the intensity variation is much smaller than the variation of antigen density recognized by the antibodies on the surface of the cells and is therefore negligible for the purpose of immunophenotyping of cells.

The surface of the slide holder 26 is aligned parallel to the CCD chip (cooled to −5° C.) of the camera and has an opening underneath the microscope slide to allow for the transmission of excitation light. The fluorescence is collected with a close-up lens 27 (f=40 mm, LM-scope), filtered with a 685/40 nm band pass filter 28 (Semrock, FF01-685/40-25), and imaged onto the chip of the CCD camera 30 with a macro lens 29 (Nikon, AF Micro-Nikkor 60 mm f/2.8D). The numerical aperture is mainly limited by the iris diaphragm of the lens, which is set to f/8. The focus ring of the lens is set such that the image has a magnification of ~1.7×. A larger aperture would result in larger angles of the light passing through the interference filter, which in turn would result in reduced suppression of the excitation light. For larger aperture settings (f#<5.6), this is visible in the corners of the image. Hence, a larger image sensor would also be problematic.

Image Analysis

After 30 min incubation at 37° C. we take one image with red and one with blue excitation light. The image analysis software is written as a platform independent ImageJ macro. Therefore any operating system that can run Java can be used for image analysis, which includes open source freeware, such as Linux as well as common smartphone operating systems (Android, Symbian, Blackberry, Windows CE), some of which are also open source. After background subtraction, regions of interest (ROIs) are identified in the sum of the two images. To be identified as a cell, an ROI has to meet several criteria, including the maximum value, the noise (variance) in the neighborhood and the size and shape of the area. The parameters to distinguish between CD4+/CD3+ (CD8+/CD3+) and CD4− (CD8−) or CD3− cells are the fluorescence intensities of APC and PerCP, respectively. The integrated intensity (after background subtraction) within an ROI for blue (red) excitation was used as the APC (PerCP) fluorescence intensity, neglecting the small overlap between the APC (PerCP) excitation spectrum and the spectrum of the excitation blue (red) excitation light. Compensation could easily be applied. However, since we do not apply gates on single parameters, compensation is not necessary in a two-parameter measurement.

Characterization

Figure 6:
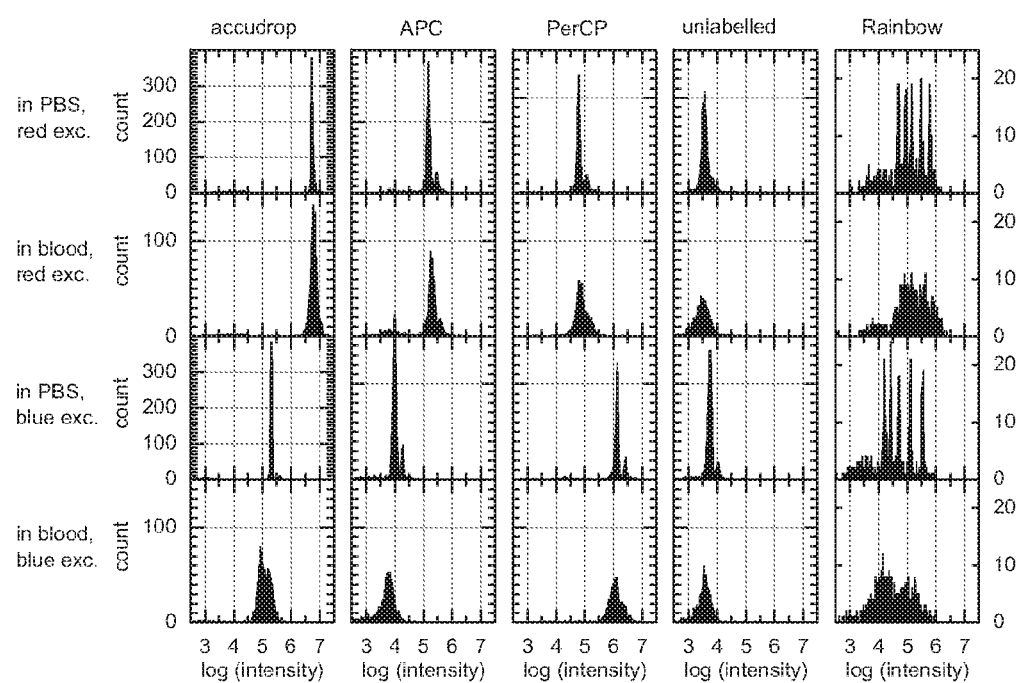
FIG. 6 shows histograms of fluorescence intensities of microbeads (Accudrop beads, APC, PerCP, unlabelled beads, and Rainbow calibration particles) suspended in PBS and whole blood. The intensities were obtained with automatic image analysis from images taken with the described system.

To characterize the imaging system, fluorescent microbeads were used. Microfluidic chambers built as described above (without the reagent layer) were filled with microbeads suspended in phosphate buffered saline (PBS) or in whole blood (90% whole blood+10% bead suspension). In FIG. 6 histograms of the fluorescence intensities of five kinds of microbeads (Accudrop, APC, PerCP, unlabelled (BD), Rainbow calibration particles (Spherotech)) for red and blue excitation are compared. The upper two rows of graphs show histograms of the detected intensities for red excitation light of beads suspended in PBS and whole blood (90% whole blood with 10% bead suspension). The lower two rows of graphs show histograms of the corresponding intensities for blue excitation light. The integration times were chosen according to the brightness of the beads between 0.2 seconds (Accudrop beads, red excitation) and 20 seconds (unlabelled beads, both colors). The coefficient of variation (CV) of the detected fluorescence intensities ranges between 6% for Accudrop beads excited with the blue LED and 20% for the unlabelled beads with red excitation. In PBS, most CVs are around 12%. In blood, the surrounding blood cells lead to a decrease of the fluorescence intensity for blue excitation light of about 30%-50%, whereas the intensities for red excitation light do not change considerably. The CVs typically increase to about 25% (red)-30% (blue), ranging from 20% (APC, red excitation) to 44% (Accudrop, blue excitation).

The detection limit of the image cytometer is about 1,000 PerCP molecules or about 5,000 APC molecules in a clear (PBS) solution. In whole blood, about 5,000 PerCP molecules or about 20,000 APC molecules can be resolved.

CD4 and CD8 T-Lymphocyte Counting

Figure 7:
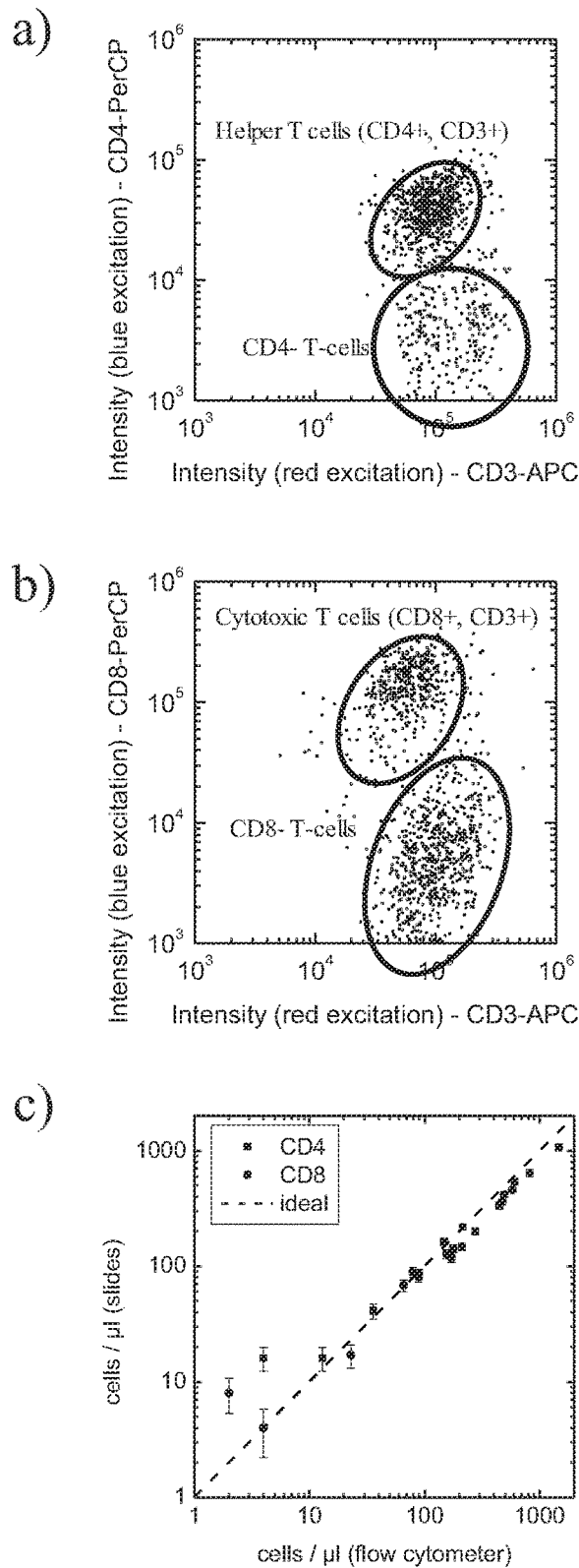
FIG. 7 shows the results of CD4 and CD8 counting experiments. a),b): Fluorescence intensities of automatically detected cells in images from slides with CD3/CD4 reagent coating (a) and CD3/CD8 reagent coating (b) after 30 min incubation with whole blood from a finger prick. Comparison of the CD4 and CD8 counts of several samples using the method of the present invention with counts obtained using flow cytometry.

T-lymphocytes express ~200,000 CD3 antigens, CD4+T-lymphocytes ~100,000 CD4 antigens and CD8+ T-lymphocytes range from 30,000 to ~500,000 CD8 antigens. Given the results described above the system should resolve CD4-PerCP, CD8-PerCP and CD3-APC labeled cells. FIG. 7 shows the scatter plots of the fluorescence intensities of automatically identified ROIs for red and blue excitation of a test chip with CD4PerCP/CD3APC (Panel a) and CDu8PerCP/CD3APC (Panel b) after filling with whole blood from a finger prick and a 30 min incubation at 37° C. In the scatter plots the CD4+ CD3+, CD4-CD3+, CD8+ CD3+ and CD8-CD3+ T-Lymphocytes can be clearly identified.

To compare with flow cytometry, in an exemplary experiment, blood from three donors was collected in EDTA collection tubes. Since donors with low CD4 counts are rare in high-income countries, low lymphocyte counts were simulated by spinning part of the initial volume of blood down (1500 rpm, 10 min), separating plasma and erythrocytes, and mixing them with the initial blood sample to prepare blood samples with lower leukocyte concentrations, but similar hematocrit value. Samples were prepared with nominal concentrations of 100%, ⅓, ⅙, and 0% of the initial concentration. For flow cytometry, 20 µl of the multi test reagent CD3-FITC, CD4-APC, CD8-PE, CD45-PerCP (BD Biosciences) were added to 50 µl of blood in a tube containing a known number of fluorescent microbeads (BD Trucount). After 15 min incubation, the erythrocytes were lysed with 450 µl of a lysing buffer (BD FACSlyse) for another 15 min. Blood from the same samples was used for the test employing the CD4/CD3 and CD8/CD3 test chambers. FIG. 7c) shows the comparison of the number of CD4 and CD8 T-lymphocytes in these samples obtained using the described slide method with flow cytometry. Apart from a few false positives and a systematic undercount of about 10-20% for high cell concentrations, the results compare very well.

Other Cell Types

The reagents contained within the gelatin solution define the targets that can be identified. For example the presence in the gelatin solution of CD20 APC present on B-lymphocytes and CD5 PerCP present on T-lymphocytes and a subset of B-lymphocytes will permit the enumeration of CD20+ CD5+ B-lymphocytes. This phenotype is associated with B-cell Chronic Lymphocytic Leukemia (B-CLL) and the frequency of these cells is associated with clinical outcome and can be used to guide therapy (Blood 2009; 113(18): 4188-4196). Another example is the presence in the gelatin solution of CD34 APC (present on hematopoietic progenitor cells and endothelial cells) and CD45 PerCP (present on leukocytes) to enumerate CD34+CD45+ hematopoietic progenitors important to determine whether a sufficient number is present for transplantation (Blood 1991; 77(2) 400-40, Biology of Blood and Marrow Transplantation 2006; 12, (1) 34-41).

While certain of the preferred embodiments of the present invention have been described and specifically exemplified above, it is not intended that the invention be limited to such embodiments. Various modification may be made thereto without departing from the spirit of the present invention, the full scope of the improvements are delineated in the following claims.

What is claimed is:

1. A method for fluorescence analysis of blood samples containing comprising:
   a. having at least one reagent comprising a fluorochrome conjugated antibody in a microfluidic chamber wherein the reagent is embedded in a dried hydrogel to provide a controlled release upon contact with the sample;
   b. filling the chamber with a blood sample containing unlysed red blood cells wherein the reagent is released from the dried hydrogel into the sample between a time required to fill the chamber and the time required to stain the cells;
   c. distributing the hydrogel containing the reagent within the chamber such that during the time required to stain the cells the released reagent is uniformly distributed within an imaging area of the chamber; and
   d. releasing the reagent from the hydrogel within the chamber in order to detect white blood cells in the blood sample wherein two fluorescent images are captured without the need to change emission filters using red (wavelength 600-800 nm) and blue (wavelength 400-500 nm) excitation light and one common emission wavelength range.

2. The method of claim 1 where the fluorochrome excited with blue light is Peridinin Chlorophyll Protein.

3. The method of claim 1 where the fluorochrome excited with red light is Allophycocyanin.

4. The method of claim 1 wherein the fluorescent images are used to determine the concentration of one or more cell phenotypes.

5. The method of claim 1 wherein the fluorescent images are used to determine the concentration of Helper T-cells (CD4+ T-lymphocytes).

6. The method of claim 1 wherein the fluorescent images are used to determine the concentration of Cytotoxic T-cells (CD8+ T-lymphocytes).

* * * * *